US006673104B2

(12) United States Patent
Barry

(10) Patent No.: US 6,673,104 B2
(45) Date of Patent: Jan. 6, 2004

(54) MAGNETIC STENT

(75) Inventor: Robert Barry, Kirkland, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 153 days.

(21) Appl. No.: 09/808,854

(22) Filed: Mar. 15, 2001

(65) Prior Publication Data

US 2002/0133219 A1 Sep. 19, 2002

(51) Int. Cl.[7] .................. A61F 2/06; A61M 37/00
(52) U.S. Cl. ............................... 623/1.15; 600/12
(58) Field of Search .................... 623/1.15, 1.34, 623/1.46; 600/9, 12

(56) References Cited

U.S. PATENT DOCUMENTS

| | | | | |
|---|---|---|---|---|
| 4,994,298 A | * | 2/1991 | Yasuda | 427/41 |
| 5,089,006 A | * | 2/1992 | Stiles | 606/198 |
| 5,431,640 A | * | 7/1995 | Gabriel | 604/270 |
| 5,908,410 A | * | 6/1999 | Weber et al. | 604/280 |
| 5,928,261 A | | 7/1999 | Ruiz | 606/200 |
| 5,951,566 A | * | 9/1999 | Lev | 606/108 |
| 5,971,967 A | * | 10/1999 | Willard | 604/264 |
| 5,989,178 A | | 11/1999 | Chiu | 600/15 |
| 6,006,756 A | * | 12/1999 | Shadduck | 128/899 |
| 6,053,873 A | * | 4/2000 | Govari et al. | 600/505 |
| 6,148,823 A | | 11/2000 | Hastings | 128/897 |
| 6,159,145 A | * | 12/2000 | Satoh | 600/12 |
| 6,206,914 B1 | * | 3/2001 | Soykan et al. | 623/1.42 |
| 2002/0022777 A1 | * | 2/2002 | Crieghton et al. | 600/407 |
| 2002/0066702 A1 | * | 6/2002 | Liu | 210/695 |
| 2002/0133225 A1 | * | 9/2002 | Gordon | 623/1.42 |

FOREIGN PATENT DOCUMENTS

| | | |
|---|---|---|
| GB | 2 352 635 A | 2/2001 |
| WO | 00/66192 | 11/2000 |
| WO | 01/28453 A2 | 4/2001 |

OTHER PUBLICATIONS

"Artificial Blood Vessel Having Magnetism", Patent Abstract of Japan, vol. 015, No. 262, Jun. 26, 1991 and JP 03 082465 A (Kanegafuchi Chem. Indu Co.
"Vascular Prosthesis Made Tube Bae Material Possess Magnetic Properties"., Database WPI, Derwent Publication, XP–002216999 & RU 2 064 784, Makhmudov S. Ya. Aug. 10, 1996.

* cited by examiner

Primary Examiner—Corrine McDermott
Assistant Examiner—Alvin Stewart
(74) Attorney, Agent, or Firm—Vidas, Arrett & Steinkraus

(57) ABSTRACT

An implantable medical device for intra lumenal support of a body lumen wherein at least a portion of the implantable medical device comprises at least one magnetic material.

10 Claims, 3 Drawing Sheets

MAGNETIC STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention is directed to implantable medical devices, such as stents, grafts, and vena-cava filters among others. Specifically, the present invention is directed to a medical device, particularly a stent, which includes in its construction or is at least partially constructed from a magnetic material, or has magnetic properties such as may be provided by a magnetic coating or other means.

2. Description of the Related Art

Stents for transluminal implantation are well known. They are generally comprised of metallic supports which are inserted into a part of the human body such as bile ducts, the urinary system, the digestive tube and notably by percutaneous route inside the blood vessels, usually the arteries in which case they are typically termed vascular stents. Stents are usually generally cylindrical and are constructed and arranged to expand radially once in position within the body. They are usually inserted while they have a first relatively small diameter and implanted in a desired area, for example inside a vessel, then the stent is expanded in situ until it reaches a second diameter larger than the first diameter.

A balloon associated with the catheter is usually used to provide the necessary interior radial force to the stent to cause it to expand radially. An example of a balloon expandable stent is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

Self-expanding stents are also known which can expand from a first diameter to a larger second diameter without the use of a means for applying an interior radial force, such as a balloon, to them. A type of self-expanding stent is described in U.S. Pat. No. 4,503,569 to Dotter which issued Mar. 12, 1985, and discloses a shape memory stent which expands to an implanted configuration with a change in temperature. Other types of self-expanding stents not made of shape memory material are also known.

The use of magnets to promote healing and reduce pain is well known in the medical profession. There have been many studies in which it has been found that the use of a magnetic field can assist in improve post operative healing. Additionally, there have been many studies in which the use of a magnetic field helps to alleviate pain due to muscle strains, tennis elbows, sore muscles, lower back pain, arthritis and the like. For example a recent study entitled *Magnetic Bio-stimulation in Painful Diabetic Peripheral Neuropathy: a Novel Intervention—a Randomized, Double-placebo Crossover Study* (American Journal of Pain Management Vol. 9 No. 1 January 1999 pgs. 8–17) illustrated the benefits of magnets in assisting in pain control and healing.

While there have been many different theories advanced as to why magnetic therapy works, it is still not clearly understood exactly how magnetic therapy aids in healing and in reducing pain. However, many devices have been developed to practice magnetic therapy. One such magnet device for therapeutic use is disclosed in U.S. Pat. No. 4,549,532, which describes a permanent magnet sheet having alternating poles for applying a magnetic field to portions of the body for therapeutic purposes. Other devices which are magnetic or include magnetic properties are described in U.S. Pat. Nos. 6,126,589; 6,066,088; 5,782,743; 5,304,111; and 5,336,498. Other medical devices which utilize magnets and magnetic fields are known.

While many prior devices which utilize magnets for improving healing are used or applied to the exterior of a body or portion thereof, there remains a need to provide for implantable medical devices which are intended to repair or support surrounding tissues with magnetic properties. As such there is a need to provide a stent with magnetic properties in order to encourage healing of a potentially damaged or weakened vessel.

The entire content of all of the patents listed within the present patent application are incorporated herein by reference.

BRIEF SUMMARY OF THE INVENTION

In light of the above, the present invention is directed to the internal application of magnetic effects by constructing a medical device, such as a stent or a portion thereof, with magnetic materials. As a result, the present invention is directed to a dual function medical device. For example, in the case of a stent, the invention provides support to a vessel or lumen, as well as providing a vessel and/or legion site with the beneficial healing effects of magnetism via the magnetic materials of the stent.

As indicated above, the present invention is directed to implantable medical devices which are constructed at least partially from magnetic materials. In the case of a stent, the stent may be entirely composed of magnetic material, or may include strips of magnetic material intertwined with conventional stent materials.

In at least one embodiment of the invention, at least the magnetic materials of the stent may be coated with a biocompatible material such as gold.

In at least one embodiment at least a portion of the stent is at least partially coated with a magnetic substance.

In at least one embodiment of the invention the various struts and members of the stent may be at least partially porous or hollow, wherein the pores or hollow chambers may be filled with a magnetic material.

In at least one embodiment of the invention the magnetic material is temporarily magnetic.

In at least one embodiment of the invention the magnetic material is permanently magnetic.

These and other more detailed and specific objectives and an understanding of the invention will become apparent from a consideration of the following Detailed Description of the Invention in view of the Drawings.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
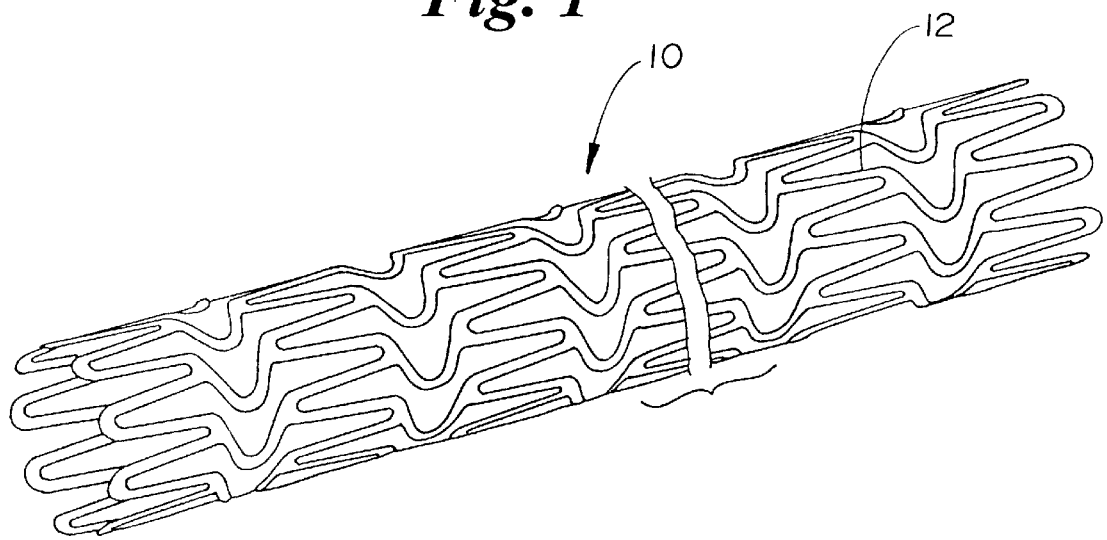
FIG. 1 is a perspective view of a first embodiment of the invention.

As may be seen in FIG. 1, the present invention is directed to an implantable medical device such as a stent 10. In the context of the present application a stent is viewed as a device for providing support or repair to a body lumen. Such devices include balloon expandable as well as self expanding stents such as have been described above, as well as stent grafts, vena cava filters, and other similar devices.

The stent 10, of the present invention may be an existing stent which is modified to include magnetic properties or may be a new stent constructed with magnetic properties as provided herein. The present invention is directed to any stent which is characterized as including in at least a portion of the stent's construction a predetermined quantity of a magnetic material or which has been rendered magnetic by any means.

The inventive stent 10 disclosed herein may be made of any stent material known in the art including polymeric materials, metals, ceramics and composites. Where the stent is made of metal, the metal may be stainless steel, elgiloy, tantalum or other plastically deformable metals. Other suitable metals include shape-memory metals such as Nitinol™.

The inventive stents may include suitable radiopaque coatings. For example, the stent 10 may be coated with gold or other noble metals or sputtered with tantalum or other metals. The stent 10 may also be made directly from a radiopaque material to obviate the need for a radiopaque coating or may be made of a material having a radiopaque inner core.

The entire stent 10, or selective portions thereof, may be manufactured from one or more magnetic materials. For example, a predetermined quantity of magnetite or an alloy thereof may be included in the construction of the stent 10. Other materials may be utilized to provide the desired magnetic properties. Such materials may be temporary magnetic materials or permanent magnetic materials. Some examples of suitable magnetic materials include, magnetic ferrite or 'ferrite' which is a substance consisting of mixed oxides of iron and one or more other metals, the heat treatment of the mixed oxides produces complex crystals with magnetic properties. An example ferrite material is: nanocrystalline cobalt ferrite, however other ferrite materials may be used. Other magnetic materials which may be utilized in the construction of stent 10 include but are not limited to: ceramic and flexible magnetic materials made from strontium ferrous oxide which may be combined with a polymeric substance such as plastic, or rubber; NdFeB (this magnetic material may also include Dysprosium); SmCo (Samarium, Cobalt); and combinations of aluminum, nickel, cobalt, copper, iron, titanium as well as other materials.

As indicated above, the beneficial nature of magnetism in healing and pain reduction is known but the mechanism which provides for these results is yet to be fully understood. However, it has been suggested that the magnetic field strength should be fairly strong in order to provide the beneficial effects desired. As a result, in the present invention, the magnet materials or magnetic properties of the stent preferably emit a magnetic field of between about 20 to 10,000 gauss and preferably between 400 and 2000 gauss.

Known stent materials such as NITINOL and stainless steel may also be rendered sufficiently magnetic by subjecting the stent material to a sufficient electric and/or magnetic field. Such a field may imbue the stent 10, or a portion thereof with magnetic properties without the need to include the magnetic materials described above in the construction of the stent 10.

As may be seen in FIG. 1, stents, such as the stent 10 presently depicted, typically are constructed of a plurality of interconnected struts and members 12. By providing one or more of the interconnected members 10 with magnetic properties a portion of the stent is rendered magnetic. Alternatively, if all of the members 12 are constructed with magnetic materials or rendered magnetic, the entire stent 10 may be provided with magnetic properties.

Figure 2:
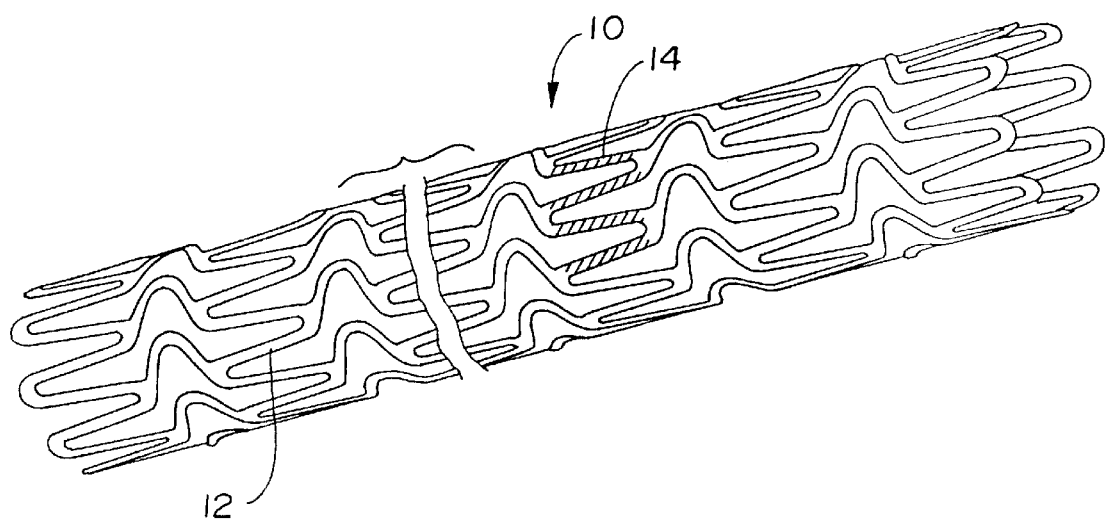
FIG. 2 is a close-up perspective view of a second embodiment of the invention.

It is understood that stent 10 is to be inserted into a body, and must therefore be biocompatible. Unfortunately, many magnetic materials may not be sufficiently biocompatible to be suitable for use in stent construction. To avoid problems associated with non-biocompatible materials, where one or more members 12 are constructed, in whole or in part, from a magnetic material which is non-biocompatible, the member 12 or a portion thereof may be coated with a biocompatible coating 14 such as may be seen in FIG. 2. The entire stent 10 or portions thereof may be coated with coating 14. Biocompatible coatings for use with stents are well known, and an example of such a coating may be gold. However, any biocompatible coating may be used with the present invention.

Figure 3:
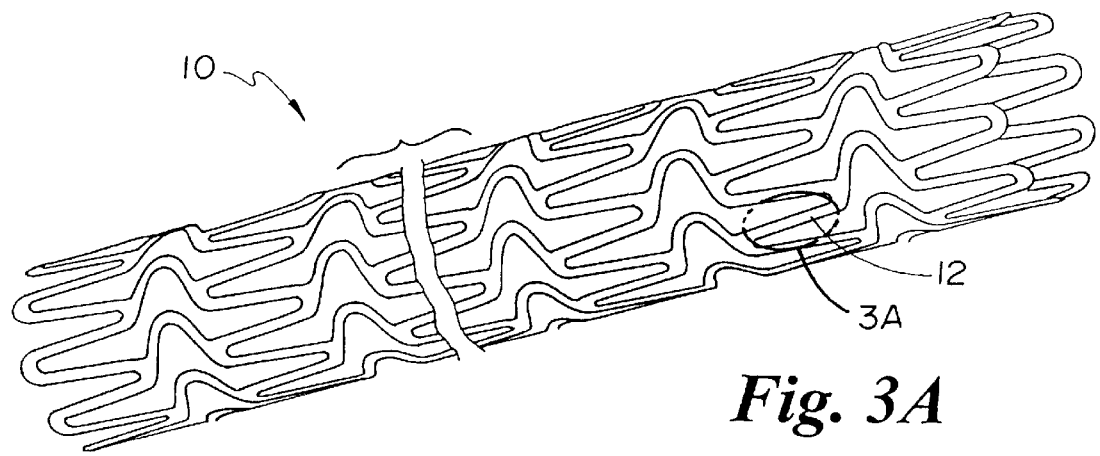
FIG. 3 is a perspective view of a third embodiment of the invention.
Figure 3A:
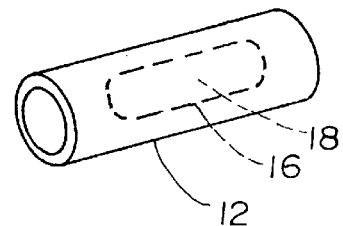
FIG. 3A is close-up view of a portion of the embodiment depicted in FIG. 3.

As may be seen in FIG. 3, the stent 10 may be configured to include magnetic material within a portion 3A of one or more of the interconnected members 12. As depicted in the detailed FIG. 3A, at least one interconnected member may include one or more chambers 16 which has a portion of magnetic material 18 contained therein. The magnetic material 18 may be in solid or liquid form. Where the stent 10 has members 12 which include chambers 16, the members 12 are preferably constructed of a biocompatible material, thus alleviating the need for an additional coating such as previously discussed.

Figure 4:
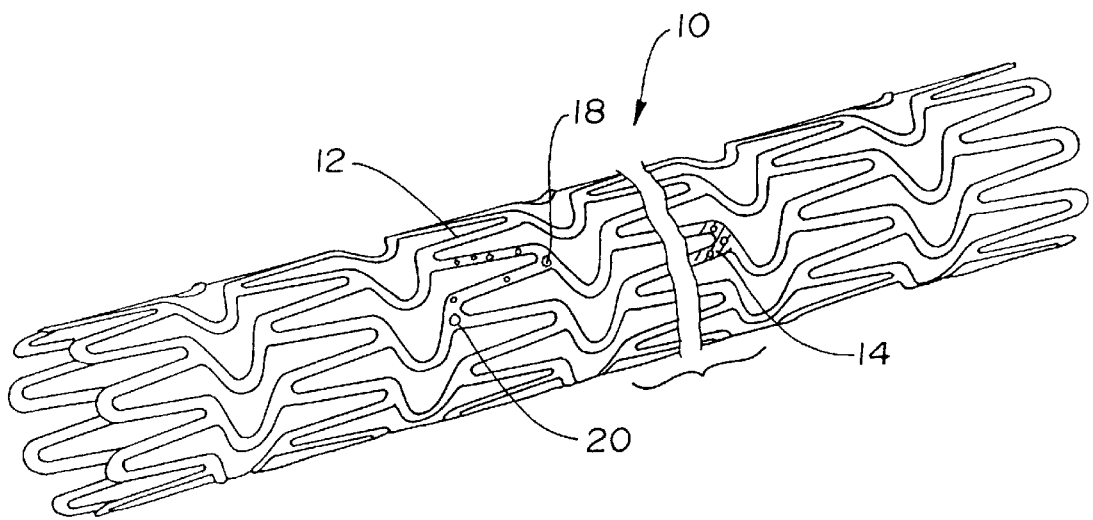
FIG. 4 is a partially exploded close-up view of a forth embodiment of the invention.

Rather than constructing specialized chambers for containing magnetic material or providing individual stent members with magnetic materials in their construction, as may be seen in FIG. 4, the members 12 of stent 10, may include one or more pores 20. The pores 20 may be filled with magnetic material 18, and then optionally coated with a biocompatible coating 14.

Figure 5:
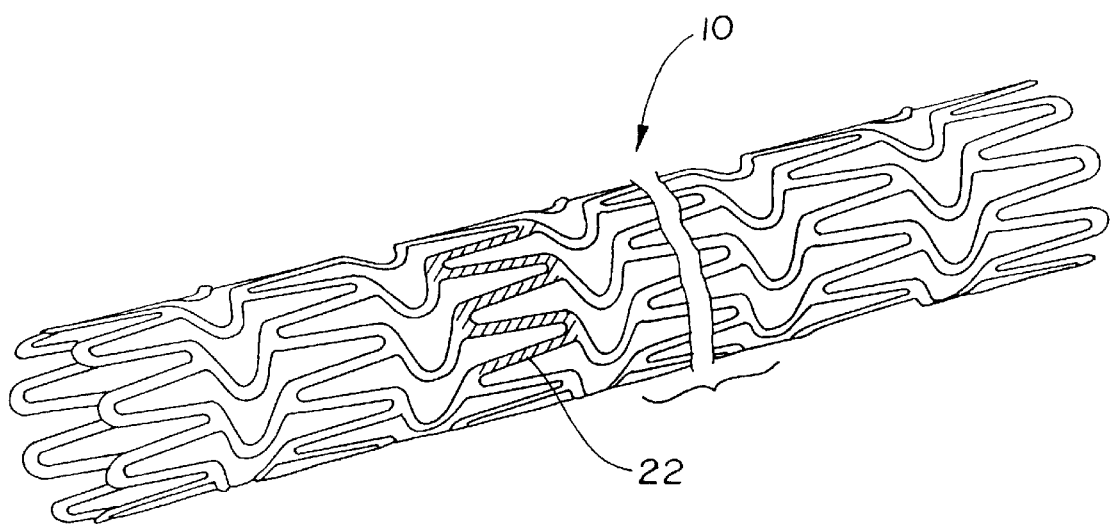
FIG. 5 is a perspective view of a fifth embodiment of the invention.

Another means of providing a stent 10 with magnetic properties may be to coat the stent 10 or a portion thereof with a coating 22 which has magnetic properties, such as is shown in FIG. 5. Such a coating may include magnetic materials such as are described above, or may be a known material which has been rendered magnetic through exposure to a magnetic and/or electric field of sufficient strength.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent for intra lumenal support of a body lumen, the entirety of the stent comprising at least one magnetic material, the at least one magnetic material being permanently magnetic, the at least one magnetic material being coated with a biocompatible material, the at least one magnetic material emitting a magnetic field, the magnetic field being between about 20–10,000 gauss.

2. The stent of claim 1 wherein the stent is selected from the group consisting of a stent-graft, vena cava filter and any combination thereof.

3. The stent of claim 1 further comprising a plurality of interconnected struts.

4. The stent of claim 3 wherein at least one of the plurality of interconnected struts is characterized as defining at least one chamber.

5. The stent of claim 3 wherein at least a portion of at least one of the plurality of interconnected struts defines at least one pore.

6. The stent of claim 1 wherein the at least one magnetic material is biocompatible.

7. The stent of claim 1 wherein the biocompatible material is selected from at least one member of the group consisting of: polymeric materials, metals, ceramics and any combination thereof.

8. The stent of claim 7 wherein the biocompatible material is selected from at least one member of the group consisting of: gold, stainless steel, elgiloy, tantalum, Nitinol, and any alloys or combinations thereof.

9. The stent of claim 1 wherein the at least one magnetic material is selected from at least one member of the group consisting of: magnetite, magnetic ferrite, strontium ferrous oxide, niobium, iron, boron, dysprosium, samarium, cobalt, aluminum, nickel, copper, titanium and any combinations and alloys thereof.

10. The stent of claim 1 wherein the predetermined magnetic field is between about 200–4000 gauss.

* * * * *